United States Patent [19]

Minami et al.

[11] 4,249,006
[45] Feb. 3, 1981

[54] METHOD OF PRODUCING 5-FLUOROURACIL DERIVATIVES

[75] Inventors: Isao Minami, Suita; Yoshio Yoshioka; Hiroaki Nomura, both of Takatsuki, all of Japan

[73] Assignee: Takeda Chemical Industries, Ltd., Osaka, Japana

[21] Appl. No.: 744,929

[22] Filed: Nov. 24, 1976

[30] Foreign Application Priority Data

Nov. 28, 1975 [JP] Japan ................................. 50-142717
Jan. 19, 1976 [JP] Japan ..................................... 51-5260
Jul. 13, 1976 [JP] Japan ................................... 51-83863

[51] Int. Cl.$^3$ .................. C07D 405/04; C07D 405/14
[52] U.S. Cl. ................................................... 544/313
[58] Field of Search ........................ 260/260; 544/313

[56] References Cited

U.S. PATENT DOCUMENTS 4,107,162  8/1978  Suzuki et al. ......................... 544/313

FOREIGN PATENT DOCUMENTS 51-23512  7/1976  Japan .

OTHER PUBLICATIONS

Brossmer et al., Chemical Abstracts, vol. 78 (1973) 58343r.
Brossmer et al., Leibigs Ann. Chem. 762, 160–166 (1972).
Chemical Abstracts, 83:193366 (1975).

*Primary Examiner*—Paul M. Coughlan, Jr.
*Attorney, Agent, or Firm*—Burgess, Ryan and Wayne

[57] ABSTRACT

A new and industrially useful method of producing 1(or 1,3-bis)-(tetrahydro-2-furyl)-5-fluorouracil or a mixture thereof by reacting 5-fluorouracil with 2,3-dihydrofuran at elevated temperature in a closed vessel. Depending upon reaction conditions, each of the above 5-fluorouracil derivatives or a mixture of them is produced.

1,3-Bis-(tetrahydro-2-furyl)-5-fluorouracil thus formed can be converted to 1-(tetrahydro-2-furyl)-5-fluorouracil by solvolysis under non-acidic conditions.

23 Claims, No Drawings

METHOD OF PRODUCING 5-FLUOROURACIL DERIVATIVES

This invention relates to a novel and industrially useful method of producing 1-(tetrahydro-2-furyl)-5-fluorouracil (may be abbreviated as mono-compound), 1,3-bis-(tetrahydro-2-furyl)-5-fluorouracil (may be abbreviated as bis-compound) or a mixture of them. Those compounds are of value as anticancer agents. The bis-compound is also useful as an intermediate for the synthesis of the mono-compound.

As a representative prior art method for production of the mono- or bis-compound, there is known a process comprising reacting 5-fluorouracil with 2-chlorotetrahydrofuran. However, the starting material 2-chlorotetrahydrofuran has industrially been produced by the addition of hydrogen chloride to 2,3-dihydrofuran.

Under the circumstances stand as above, the present inventors have made extensive studies to produce the present compounds with the use of 2,3-dihydrofuran as a starting material. The studies led us to an unexpected finding that when 5-fluorouracil and 2,3-dihydrofuran are heated together at an elevated pressure, the mono- or bis-compound or their mixture is produced in unusually high yield.

The present inventors found also that the bis-compound, which is produced as above and may be a mixture with the mono-compound, is converted to the mono-compound by solvolysis under non-acidic conditions.

An object of the present invention is to provide an industrially simple and practical method of producing the mono- or bis-compound or their mixture. Another object of the invention is to provide a method for producing the mono-compound by subjecting the bis-compound, which is produced as above and may be a mixture with the mono-compound, to solvolysis under non-acidic conditions.

The present invention is directed to a method for producing the mono- or bis-compound or a mixture thereof which comprises reacting 5-fluorouracil with 2,3-dihydrofuran in a closed vessel under heating.

And a part of this invention is directed to a method of producing the mono-compound which comprises subjecting the bis-compound as produced above to solvolysis under non-acidic conditions.

According to the present invention the mono- or bis-compound or a mixture thereof is produced by reacting 5-fluorouracil with 2,3-dihydrofuran at elevated temperature in a closed vessel.

The heating temperature is normally within the range of about 100° to 250° C. The preferable temperature to form the mono-compound is between about 150° and 200° C. and more preferably between about 165° and 185° C. The bis-compound may be formed at a temperature between about 125° and 200° C., preferably between about 125° and 180° C. and more preferably between about 135° and 165° C.

Production of the mono-compound tends generally to increase at a temperature higher than about 180° C., and at a lower temperature, that of the bis-compound tends to rise.

The reaction temperature may be selected from the above ranges according to the kind of solvent, reaction scale, reaction time and other conditions, trial runs being used with advantage for selecting the optimum temperature.

As the closed reaction vessel, an autoclave may be used.

This reaction may be carried out in the presence of a solvent. While one of the starting materials, i.e., 2,3-dihydrofuran, may be used as the solvent as well, it is possible to employ another suitable solvent which is free of active hydrogen, such as amides (e.g. dimethylformamide, dimethylacetamide, hexamethylphosphoramide, etc.), ethers (e.g. tetrahydrofuran, dioxane, etc.), tertiary amines (e.g. pyridine, triethylamine, etc.), esters (e.g. ethyl formate, ethyl acetate, etc.) and a suitable mixture of such solvents.

In general, it is preferably to carry out the reaction using a mole excess of 2,3-dihydrofuran over 5-fluorouracil.

For the purpose of producing predominantly the mono-compound, the molar ratio of 2,3-dihydrofuran to 5-fluorouracil may be selected from the range of about 2 to 8 and, preferably, from the range of about 4 to 6.

And, in order to produce mainly the bis-compound, it is advantageous to charge the solvent with both 5-fluorouracil and 2,3-dihydrofuran in high concentration. For example, the solvent may be employed ina proportion not exceeding about 15 times (v/w), preferably about 8-1.5 times (v/w) the amount of 5-fluorouracil. 2,3-Dihydrofuran may be employed in a proportion generally not less than about 3 mols, preferably in about 3.5-10 mols based on 1 mol of 5-fluorouracil. It is preferable to increase a proportion of 2,3-dihydrofuran to 5-fluorouracil when a large amount of solvent is employed.

Such a proportion as mentioned above may be selected experimentally in consideration of the kind and amount of solvent, reaction temperature and other conditions.

Namely, when the reaction time is sufficient the bis-compound is produced in better yield in proportion to the molar concentration of 2,3-dihydrofuran at a temperature between 135° and 165° C. The formation rate of the mono-compound to bis-compound varies with the reaction time.

In the case of producing the mono-compound directly from 5-fluorouracil, it is preferable to stop the reaction as soon as the bis-compound is detected by thin-layer chromatography on silica gel.

To produce the bis-compound a prolonged reaction time, for example, more than 4 hours is preferable at about 150° C. In shorter reaction period the production of the bis-compound is rather small. Especially when a solvent is employed in a rather small amount, a longer reaction time is preferable.

The contemplated compound thus obtained can easily be separated from the reaction mixture in a conventional manner.

For example, the desired compound may be separated by the procedure of concentrating the reaction mixture to dryness under reduced pressure, extracting the residue with a solvent and removing the solvent by distillation. As a solvent of recrystallization for the mono-compound ethanol is preferable and petroleum ether is preferable for the bis-compound.

In order to produce the mono-compound, even where the reaction product mixture contains not only the bis-compound but also the mono-compound, it is possible to subject the reaction mixture to solvolysis under non-acidic condition without separating the mono-compound. The bis-compound may be subjected to solvolysis after it has been isolated or, without prior isolation, as the resultant reaction mixture per se. This procedure may be accomplished merely by heating the bis-compound with water or a water-containing solvent (such as aqueous methanol, ethanol, pyridine, dioxane, tetrahydrofuran, acetone, etc.) under non-acidic conditions.

In the presence of an acid, fixing of the reaction condition is difficult, because the reaction rate of the solvolysis is too fast. Namely, it is hard to stop the reaction at the time when the bis-compound has disappeared and has been converted into the mono-compound, whereas 5-fluorouracil has not appeared yet in the reaction mixture. And the acid used may be included as an impurity in the product of the mono-compound. Therefore, addition of an acid into the reaction mixture is generally disadvantageous and solvolysis under neutral or basic conditions is favorable.

Generally the solvolysis proceeds well under heating (e.g. at about 40°–80° C.). For example, where an aqueous alcohol is employed, the reaction temperature is desirably within the range of about 50° C. to the reflux temperature of the reaction system. But, the reaction may occasionally proceed without heating.

Preferable water-containing solvents contain in many cases water not more than 50% (v/v), though an solvents containing more water may occasionally be used. For example, the aqueous alcohol preferably contains about 40 to 80 percent (v/v) of alcohol.

The present solvolysis proceeds under non-acidic conditions as mentioned above and so produces the desired mono-compound of high purity in a good yield with simple and convenient procedure. The mono-compound produced in the above manner may be separated by conventional means, for instance, by distilling off solvent from the resultant reaction mixture.

The bis-compound produced in the present process is not only of value as an intermediate for producing the mono-compound, but also as an anticancer agent, having an effect on prolonging survival time of p-388 leukemia bearing mice.

The method according to this invention has the following technical advantages:

(1) The contemplated compound can be produced in good yield and high purity.
(2) Industrial production of 2-chlorotetrahydrofuran, a starting material for the aforesaid prior art process, has been produced by reacting 2,3-dihydrofuran, which is a starting material for this invention, with hydrogen chloride. Therefore, compared with the above known process, the method according to this invention has more advantage of substantially fewer reaction steps and lower cost as well.
(3) Whereas 2-chlorotetrahydrofuran, which is employed in the known process, is chemically unstable, 2,3-dihydrofuran to be employed according to this invention is chemically stable. Therefor, the method according to this invention employing the latter compound is more advantageous in respect of reaction procedure.
(4) Whereas, in the above prior art method the contemplated compound tends to be decomposed by the hydrochloric acid by-product no such decomposition of the contemplated compound takes place in the method of this invention.
(5) Since the amount of by-product is small as compared with the known process, the contemplated compound can be more easily isolated by the present process.

In the following examples, yields may be improved by repeating the experiments.

EXAMPLE 1

To 30 ml of pyridine was added 1.3 g of 5-fluorouracil together with 2.8 g of 2,3-dihydrofuran and, in a closed tubular reactor, the resultant mixture was heated at 185° C. for 8 hours. After cooling, the reaction mixture was concentrated to dryness under reduced pressure and the residue was recrystallized from 5 ml of ethanol. By the above procedure was obtained 1.3 g colorless needles of 1-(tetrahydro-2-furyl)-5-fluorouracil, melting point: 164°–168° C.

In thin-layer chromatography on silica gel (solvent system: methanol-chloroform=1:9), this product gave a single U.V. spot. The I.R., NMR and UV spectra of this product were also measured and confirmed to agree with the corresponding species of an authentic sample.

Elemental analysis:
Calcd. for $C_8H_9O_3N_2F$: C, 47.99; H, 4.50; N, 14.00.
Found: C, 47.55; H, 4.83; N, 13.82.

EXAMPLE 2

To 20 ml of N,N-dimethylformamide was added 0.5 g of 5-fluorouracil together with 2.3 g of 2,3-dihydrofuran and, in a closed tubular reactor, the mixture was heated at 185° C. for 4 hours. After cooling, the reaction mixture was concentrated to dryness under reduced pressure and the residue was recrystallized from ethanol. By the above procedure was obtained 0.4 g colorless-crystals of 1-(tetrahydro-2-furyl)-5-fluorouracil, melting point: 164°–168° C. EXAMPLE 3

To 30 ml of pyridine was added 1.0 g of 5-fluorouracil together with 2.69 g of 2,3-dihydrofuran and, in a closed tubular reactor, the mixture was heated at 170° C. for 10 hours. Thereafter, the reaction mixture was treated in the same manner as the foregoing examples to obtain 0.984 g colorless needles of the desired product. In thin layer chromatography on silica gel, this product gave a single spot at the same $R_f$ as did an authentic sample.

It should be understood that the yields given in the above examples may be further improved by repeating trial runs.

EXAMPLE 4

In a closed tubular reactor, 1.3 g of 5-fluorouracil, 6.5 ml of pyridine and 7.0 g of 2,3-dihydrofuran were heated together at 200° C. for 6 hours. After cooling, the reaction mixture was concentrated to dryness under reduced pressure and the residue was suspended in 10 ml of ethyl ether. The suspension was stirred for a while, after which the insolubles were filtered off.

The ethereal mother liquor was concentrated to about 5 ml and, then, 50 ml of petroleum ether was added dropwise, whereupon 1.5 g of 1,3-bis-(tetrahydro-2-furyl)-5-fluorouracil was obtained as a precipitate, melting point: 98° C.

Elemental analysis:
Calcd. for $C_{12}H_{15}FN_2O_4$: C, 53.33; H, 5.59; N, 10.36; F, 7.03.
Found: C, 53.42; H, 5.89; N, 9.98; F, 7.01.
Ultraviolet absorption spectrum: $\lambda_{max}$MeOH 274 m$\mu$ NMR absorption spectrum: (60 Mc, CDCl$_3$): δ7.33, 1 H, (d, J=6Hz), δ6.58, 1 H, t. δ5.97, 1 H, m. δ3.67–4.50, 4 H, m. δ1.67–2.67, 8 H, m.

EXAMPLE 5

In a closed tubular reactor, 1.3 g of 5-fluorouracil, 5 ml of benzene and 14 g of 2,3-dihydrofuran were heated together at 200° C. for 6 hours. After cooling, the reaction mixture was concentrated to dryness under reduced pressure and the residue was separated and purified by column chromatography on 25 g silica gel. From the chloroform eluate, the fractions rich in the contemplated compound were collected. The solvent was distilled off and the residue was recrystallized from petroleum ether. By the above procedure was obtained 1.3 g of 1,3-bis-(tetrahydro-2-furyl)-5-fluorouracil.

EXAMPLE 6

In an autoclave, 520 g of 5-fluorouracil, 1400 g of 2,3-dihydrofuran and 1.56 l of pyridine were heated together at 185° C. for 3 hours. After cooling, the reaction mixture was concentrated to dryness under reduced pressure and the residue was dissolved in 6 l of ethanol-water(1:1). The solution was heated at 70° C. for 2 hours, after which it was treated with activated charcoal. After filtration, the solution was concentrated under reduced pressure to about one-half of its original volume. After cooling, the resultant crystals were recovered by filtration and dried. By the above procedure was obtained 780 g of 1-(tetrahydro-2-furyl)-5-fluorouracil. If necessary, this product may be recrystallized from ethanol. Recrystallization yielded 600 g of colorless needles, melting point: 167.5° C.

Elemental analysis:
Calcd. for C$_8$H$_9$FN$_2$O$_3$: C, 48.00; H, 4.53; N, 13.99.
Found: C, 47.93; H, 4.52; N, 13.85.

EXAMPLE 7

Synthesis of 1,3-bis-(tetrahydro-2-furyl)-5-fluorouracil

In 20.8 ml of pyridine were dissolved 5.2 g (40 m mol) of 5-fluorouracil and 14 g (200 m mol) of 2,3-dihydrofuran. The solution were heated at about 150° C. in a closed tubular reactor under agitation for 6 hours. After the reaction, the reaction mixture was concentrated to dryness under reduced pressure. The residue was dissolved in chloroform and the solution was passed through a column of silica gel. The column was eluated with chloroform and the effluent was concentrated to dryness under reduced pressure. The residue was washed with a small amount of petroleum ether to give the above-mentioned compound as colorless crystals.

Yield, 9.2 g (85%), melting point: 98° C.

EXAMPLE 8

Synthesis of 1,3-bis-(tetrahydro-2-furyl)-5-fluorouracil

In 20.8 ml of pyridine were dissolved 5.2 g (40 m mol) of 5-fluorouracil and 9.8 g (140 m mol) of 2,3-dihydrofuran. The solution was heated at about 160° C. in a closed tubular reactor under agitation for 5 hours. The resultant reaction mixture was treated similarly to Example 7 to give the above mentioned-compound.

Yield, 7.67 g (71%), melting point: 98° C.

EXAMPLE 9

Synthesis of 1-(tetrahydro-2-furyl)-5-fluorouracil

In 20.8 ml of pyridine were dissolved 5.2 g (40 m mol) of 5-fluorouracil and 9.8 g (140 m mol) of 2,3-dihydrofuran. The solution was heated at about 150° C. in a closed tubular reactor under agitation for 6 hours. The resultant reaction mixture was concentrated to dryness under reduced pressure. The residue was dissolved in 50% aqueous ethanol and heated at 70° C. After the reaction, the solution was concentrated to dryness under reduced pressure. Recrystallization of the residue from 90% ethanol gives 6.56 g of colorless crystals.

Yield, 82%, melting point: 168° C.

We claim:

1. A method for producing 1-(tetrahydro-2-furyl)-5-fluorouracil, 1,3-bis-(tetrahydro-2-furyl)-5-fluorouracil or a mixture thereof which comprises heating a reaction mixture comprising 5-fluorouracil and 2,3-dihydrofuran, in a closed vessel.

2. A method according to claim 1 wherein the reaction is conducted in the presence of a solvent which is free of active hydrogen or a mixture of such solvents.

3. A method according to claim 2 wherein the solvent is excess 2,3-dihydrofuran.

4. A method according to claim 1 wherein the reaction temperature is between about 100° and 250° C.

5. A method according to claim 1 wherein a molar excess of 2,3-dihydrofuran to 5-fluorouracil is employed.

6. A method according to claim 1 wherein 1-(tetrahydro-2-furyl)-5-fluorouracil is produced by conducting the reaction at a temperature between about 150° and 200° C.

7. The method of claim 6 wherein the reaction temperature is between about 165° C. and 185° C.

8. A method according to claim 1 wherein 1-(tetrahydro-2-furyl)-5-fluorouracil is produced by employing a molar ratio of 2,3-dihydrofuran to 5-fluorouracil of between about 2 and 8.

9. A method according to claim 8 wherein the molar ratio is between about 4 and 6.

10. A method according to claim 1 wherein 1-(tetrahydro-2-furyl)-5-fluorouracil is produced by stopping the heating on detecting the presence of 1,3-bis-(tetrahydro-2-furyl)-5-fluorouracil.

11. A method according to claim 1 wherein 1,3-bis-(tetrahydro-2-furyl)-5-fluorouracil is produced by maintaining the reaction temperature between about 125° and 200° C.

12. A method according to claim 11 wherein the reaction temperature is maintained between about 135° and 165° C.

13. A method according to claim 12 wherein the reaction is conducted for a period of at least 4 hours.

14. A method according to claim 2 for producing 1,3-bis-(tetrahydro-2-furyl)-5-fluorouracil wherein the volume/weight ratio expressed as ml/g of the solvent to 5-fluorouracil does not exceed about 15:1.

15. A method according to claim 14 wherein the ratio is between about 8 and 1.5:1.

16. The method of claim 1 for producing 1,3-bis-(tetrahydro-2-furyl)-5-fluorouracil wherein the molar ratio of 2,3-dihydrofuran to 5-fluorouracil is at least about 3:1.

17. The method of claim 16 wherein the ratio is between about 3.5 and 10:1.

18. A method for producing 1-(tetrahydro-2-furyl)-5-fluorouracil, according to claim 1 which comprises heating the reaction mixture at a temperature in excess of about 180° C.

19. A method for producing 1-(tetrahydro-2-furyl)-5-fluorouracil comprising hydrolyzing 1,3-bis-(tetrahydro-2-furyl)-5-fluorouracil with water or aqueous alcohol under neutral conditions.

20. A method according to claim 19 wherein the hydrolyzing is effected by heating at a temperature between about 40° and 80° C.

21. A method according to claim 20 wherein the solvent is water and ethanol in a 1:1 volume ratio.

22. A method according to claim 1 wherein the reaction mixture containing 1,3-bis-(tetrahydro-2-furyl)-5-fluorouracil is solvolyzed, under non-acidic conditions, to obtain 1-(tetrahydro-2-furyl)-5-fluorouracil.

23. A method for producing 1-(tetrahydro-2-furyl)-5-fluorouracil which comprises heating a reaction mixture comprising 5-fluorouracil and 2,3-dihydrofuran in a closed vessel.

* * * * *

UNITED STATES PATENT AND TRADEMARK OFFICE
CERTIFICATE OF CORRECTION

PATENT NO. : 4,249,006

DATED : Feb. 3, 1981

INVENTOR(S) : Isao Minami, et al

It is certified that error appears in the above—identified patent and that said Letters Patent is hereby corrected as shown below:

Column 1, line 20: "stand as above" should be --as stated above--

Column 2, line 25: "ina" should be --in a--.

Column 3, line 27: "an" should be --any--.

Column 4, line 36: "EXAMPLE 3" should be set out in a new paragraph.

Signed and Sealed this

Eleventh Day of August 1981

[SEAL]

Attest:

Attesting Officer

GERALD J. MOSSINGHOFF

Commissioner of Patents and Trademarks